(12) United States Patent
Makimura (10) Patent No.: US 8,512,496 B2
(45) Date of Patent: Aug. 20, 2013

(54) ELASTIC MEMBER GUIDE DEVICE AND MANUFACTURING METHOD OF DISPOSABLE WEARING ARTICLES

(75) Inventor: Kazutoshi Makimura, Settsu (JP)

(73) Assignee: Zuiko Corporation, Osaka (JP)

(*) Notice: Subject to any disclaimer, the term of this patent is extended or adjusted under 35 U.S.C. 154(b) by 345 days.

(21) Appl. No.: 12/990,657

(22) PCT Filed: May 22, 2009

(86) PCT No.: PCT/JP2009/059426
§ 371 (c)(1),
(2), (4) Date: Nov. 2, 2010

(87) PCT Pub. No.: WO2009/147957
PCT Pub. Date: Dec. 10, 2009

(65) Prior Publication Data
US 2011/0048618 A1   Mar. 3, 2011

(30) Foreign Application Priority Data
Jun. 4, 2008 (JP) .................................. 2008-146535

(51) Int. Cl.
*A61F 13/15* (2006.01)
*B32B 37/00* (2006.01)

(52) U.S. Cl.
USPC ........... 156/161; 156/229; 156/494; 156/495; 156/496

(58) Field of Classification Search
USPC .................. 156/229, 161, 163, 164, 494, 495, 156/496
See application file for complete search history.

(56) References Cited

U.S. PATENT DOCUMENTS

| 6,585,841 B1 * | 7/2003 | Popp et al. .................... 156/161 |
| 6,895,649 B2 * | 5/2005 | Kojo et al. ................... 29/407.01 |
| 2005/0098259 A1 | 5/2005 | Otsubo et al. |

FOREIGN PATENT DOCUMENTS

| JP | 4-317649 | 11/1992 |
| JP | 2003-299691 | 10/2003 |
| JP | 2004-073427 | 3/2004 |
| JP | 2006-230833 | 9/2006 |

OTHER PUBLICATIONS

Machine translation of Japanese Patent 2006-203833, date unknown.*
International Search Report issued Aug. 18, 2009 in International (PCT) Application No. PCT/JP2009/059426.

* cited by examiner

*Primary Examiner* — Jeff Aftergut
(74) *Attorney, Agent, or Firm* — Wenderoth, Lind & Ponack, L.L.P.

(57) ABSTRACT

An elastic member drive device includes: a drive shaft 12*a* that allows a plurality of pulleys 21, 31 and 41 to be removably attached as being coaxially aligned in the rotation center axis direction; transmission belts 23, 33 and 43 that are respectively wound around pulleys 21, 31 and 41; and a driver portion 12 that controls regular and reverse rotations of the drive shaft 12*a*, wherein the guides 25, 35 and 45 are respectively fixed to the transmission belts 23, 33 and 43. A feed amount difference in the web width direction is allowed to be set for each of the guides 25, 35 and 45 by determining a pulley diameter ratio among the pulleys 21, 31 and 41.

4 Claims, 5 Drawing Sheets

ELASTIC MEMBER GUIDE DEVICE AND MANUFACTURING METHOD OF DISPOSABLE WEARING ARTICLES

TECHNICAL FIELD

The present invention relates to a technique of fixing elastic members in an expanded state to a web to manufacture a shrinkable web.

BACKGROUND ART

Conventionally, what has been practiced is to continuously feed a plurality of elastic members in an expanded state, and fix them to a continuously fed web's one surface at a plurality of places at intervals in the web width direction, to thereby drastically enhance the shrinkage of the web. Here, in order to control a positional range, a direction and the like that enhance the shrinkage of the web, sometimes intervals at which the elastic members are paralleled adjacent to one another in the web width direction are varied. In this case, the paralleled intervals are varied by forcibly changing the positions (fixed positions) where the elastic members are brought into contact with the web's one surface.

Conventionally, in order to control the paralleled intervals, what has been used is an elastic member guide device that includes a guide having a plurality of guide holes, with one elastic member passed through each guide hole. The shaft that supports the guide is driven to perform a prescribed reciprocating motion in the web width direction by a traverse cam. The fixed position intervals among the elastic members are varied by moving the guide in the web width direction.

However, Japanese Patent Laid-Open Publication No. 4-317649 (FIG. 6, paragraph Nos. 0013 and 0015 to 0018) does not specifically disclose how the guide should be moved in the web width direction for widening the fixed position intervals of the elastic members, which are merely passed through respective holes provided at one identical guide. Even if the momentum of the reciprocating motion of the guide is used to dispersedly arrange the elastic members, it is difficult to form an estimation of the extent of the dispersion, and hence, adjustment must be carried out through repetition of trial and error. Further, control of the extent of the dispersion based solely on the reciprocating motion of the guide is limited, and the range in which the fixed position intervals in the web width direction among the elastic members is also limited.

SUMMARY OF THE INVENTION

In consideration of the circumstances described in the foregoing, an object of the present invention is, when continuously feeding a plurality of elastic members in an expanded state and fixing them to a continuously fed web's one surface at a plurality of places at intervals in the web width direction, to carry out setting of varying the fixed position intervals in the web width direction freely and easily.

In order to achieve the object stated above, the present invention provides an elastic member guide device, including guides that each allow an elastic member being continuously fed in an expanded state to pass through, wherein a position where the elastic member is brought into contact with one surface of a web being continuously fed is varied in a web width direction by a controlled shift of the guides, wherein the elastic member guide device comprises a drive shaft that allows a plurality of pulleys to be removably attached thereto while being coaxially aligned in a rotation center axis direction, transmission belts that are respectively wrapped around the pulleys, and a driver portion that controls regular and reverse rotations of the drive shaft, wherein the guides are respectively fixed to the transmission belts, and wherein a feed amount difference in the web width direction is allowed to be set for each of the guides, by determining a pulley diameter ratio among the plurality of pulleys.

In the present invention, the "web" refers to a planar film, a fibrous product and the like. Further, the "elastic member" refers to a member that is elastic and is capable of enhancing the shrinkage of the web in a state being fixed to the web's one surface while maintaining its expanded state.

With the structure of the present invention, it is possible to attach a plurality of pulleys aligned in a coaxial manner to a drive shaft, and to simultaneously rotate the pulleys with the single drive shaft. Because the driver portion is capable of exerting the regular and reverse rotation control of the drive shaft, it is possible to secure synchronization of actuation and stop as to the guides driven by the same drive shaft, and to freely cause the guides to perform the reciprocating motion. It goes without saying that each of the transmission belts is wrapped around each pulley and its paired follower pulley.

Because the transmission belts can be used in an oilless manner, being different from transmission chains that require oil supply, they will not soil the web even when they are disposed on the conveyer line of the web.

Because the guides are fixed to the transmission belts, the elastic members continuously fed in an expanded state can respectively be guided in the web width direction by the guides.

Because the feed amount of each transmission belt is determined depending on a pulley diameter, provision of a pulley diameter ratio among a plurality of pulleys that rotate coaxially and in synchronization with one another makes it possible to differ the feed amount in the web width direction of each guide relative to the rotation amount of the drive shaft, among the guides.

A plurality of pulleys can removably be attached to the drive shaft with a determined pulley diameter ratio among them. Accordingly, a fixed position interval in the web width direction between the elastic member guided by one guide and the elastic member guided by other guide is widened or narrowed in accordance with the pulley diameter ratio when the driver portion rotates the drive shaft in one of regular and reverse directions, and is narrowed or widened in accordance with the pulley diameter ratio when the driver portion rotates the drive shaft in the other one of the regular and reverse directions.

Thus, according to the present invention, the fixed position interval between the elastic members guided by the guides can freely and easily be set by the numerical design of each pulley diameter ratio and control of the regular and reverse rotations of the drive shaft.

The elastic member guide device according to the present invention is applicable to a manufacturing method of disposable wearing articles. As used herein, a disposable wearing article refers to a disposable sanitary article in which a waist portion, a connection portion, and a right and left pair of leg-inserting holes are formed. The waist portion refers to a portion having a web width spanning over the entire circumference of the waist when worn. The waist portion may be formed in any one of the following structures: a structure previously continuously formed over the entire circumference as in an underpants-type paper diaper; and a structure to be worn as being connected to be continuous as in a tape-type paper diaper. The connection portion refers to a portion where an absorber for receiving body wastes is fixed, and that connects between the abdominal side and the back side of the waist portion. The connection portion may be formed in any one of the following structures: a structure continuously formed from the waist portion; and a structure in which the connection member having the absorber fixed thereto is bridged between the back side and the abdominal side of the waist portion. Right and left refers to the right and left directions when the disposable wearing article is seen from the front (abdominal side).

The manufacturing method of the disposable wearing articles is based on what is called a transverse flow manufacturing method or a longitudinal flow manufacturing method.

The transverse flow manufacturing method refers to a manufacturing method in which the waist portion is gradually formed from the downstream side, having its right to left width direction agreed with the feed direction of the web. The back side and the abdominal side of the waist portion can integrally, or separately, be formed as to the continuously fed web. In a case where they are integrally formed, the back side is formed using the web-width directional one end side of the web, and the abdominal side is formed using the other end side. In a case where they are separately formed, only one of the abdominal and back sides is formed as to a first web being continuously fed, and then only the other one of the abdominal and back sides is formed as to a second web being continuously fed in a separate manner; alternatively, the back side and the abdominal side can be formed so as to alternate in the feed direction in both the first web and the second web.

On the other hand, the longitudinal flow manufacturing method refers to a manufacturing method in which the back side and the abdominal side of the waist portion are formed so as to alternate from the downstream side as to a continuously fed web, having its right to left width direction agree with the web width direction.

The transverse flow and longitudinal flow manufacturing methods each include a step of fixing continuously fed elastic members in an expanded state to a continuously fed web's one surface, for the purpose of enhancing the fit at the waist portion. The elastic member provided for this purpose exists at least one in number, and enhances the shrinkage of the waist portion in the circumferential direction. The elastic member for this purpose can continuously be fixed in the feed direction of the web, when the transverse flow manufacturing method is employed. On the other hand, the elastic member is intermittently supplied and fixed at intervals in the feed direction when the longitudinal flow manufacturing method is employed.

The longitudinal flow manufacturing method includes a step of partially cutting the web in the feed direction at regular intervals, so as to form each right and left pair of leg-inserting holes.

In some cases, the transverse flow manufacturing method also includes the step of partially cutting the web in the feed direction at regular intervals, so as to form the entire rim portion of the right and left pair of leg-inserting holes, or to form the rim portion except for the portion formed with the connection member.

In a case where the leg-inserting holes are formed in the manner described above, the following steps may be included: a step of fixing an elastic member to the web's one surface in a wavy manner so as to swing in the web width direction and with periodicity in the feed direction; and a step of forming a rim portion of each of the leg-inserting holes such that a cut portion along the elastic member is generated. The elastic member fixed in a wavy manner exists at least one in number. In any of the transverse flow manufacturing method and the longitudinal flow manufacturing method, employing both the steps makes it possible to provide a region where the elastic member is present along the rim portion of each leg-inserting hole, so as to enhance the fit in the rim portion in each leg-inserting hole, and to eventually prevent the article from coming off when worn.

Here, in a case where the longitudinal flow manufacturing method is employed, or in a case where the transverse flow manufacturing method is employed to form the abdominal and back sides of the waist portion using the opposite sides in the web width direction of the web, a plurality of elastic members fixed in a wavy manner may be fixed such that a swing difference between each adjacent ones of elastic members becomes greater as becoming near to the center of the connection portion (for example, see Japanese Patent Laid-Open Publication No. 4-317649 (FIG. 6, paragraph Nos. 0013 and 0015 to 0018)). Thus, the fit near the crotch and the rim portions of the leg-inserting holes where leakage of body wastes is prone to occur can drastically be enhanced, whereby the anti-leak characteristic can be improved.

As described above, in fixing a plurality of elastic members in a wavy manner, or in fixing a plurality of elastic members for enhancing the fit at the waist portion, it is possible to use the elastic member guide device according to the present invention, to guide the elastic members respectively by the separate guides, and to set the swing for each of the elastic members based on pulley diameters.

A plurality of elastic members are fixed in a wavy manner with prescribed periodicity in the feed direction by regular and reverse rotation control exerted over the drive shaft. Here, the fixed positions in the web width direction of the elastic members are varied in the web width direction in synchronization with one another. Accordingly, by setting the swing for each of the elastic members based on the pulley diameters, the fixed position intervals can be controlled.

The plurality of elastic members may be the ones for the purpose of enhancing the fit at the waist portion, and/or the ones for the purpose of enhancing the fit at the rim portion of each leg-inserting hole.

As described in the foregoing, the elastic member guide device according to the present invention makes it possible to freely and easily set the fixed position intervals among the elastic members by the numerical design of the pulley diameter ratio and the regular and reverse rotation control of the drive shaft. Accordingly, in continuously feeding a plurality of elastic members in an expanded state, and fixing them to the continuously fed web's one surface at a plurality of places at intervals in the web width direction, setting of varying the fixed position intervals in the web width direction can freely and easily be carried out.

DETAILED DESCRIPTION OF THE INVENTION

In the following, a description will be given of embodiments of the present invention with reference to the drawings.

Figure 1:
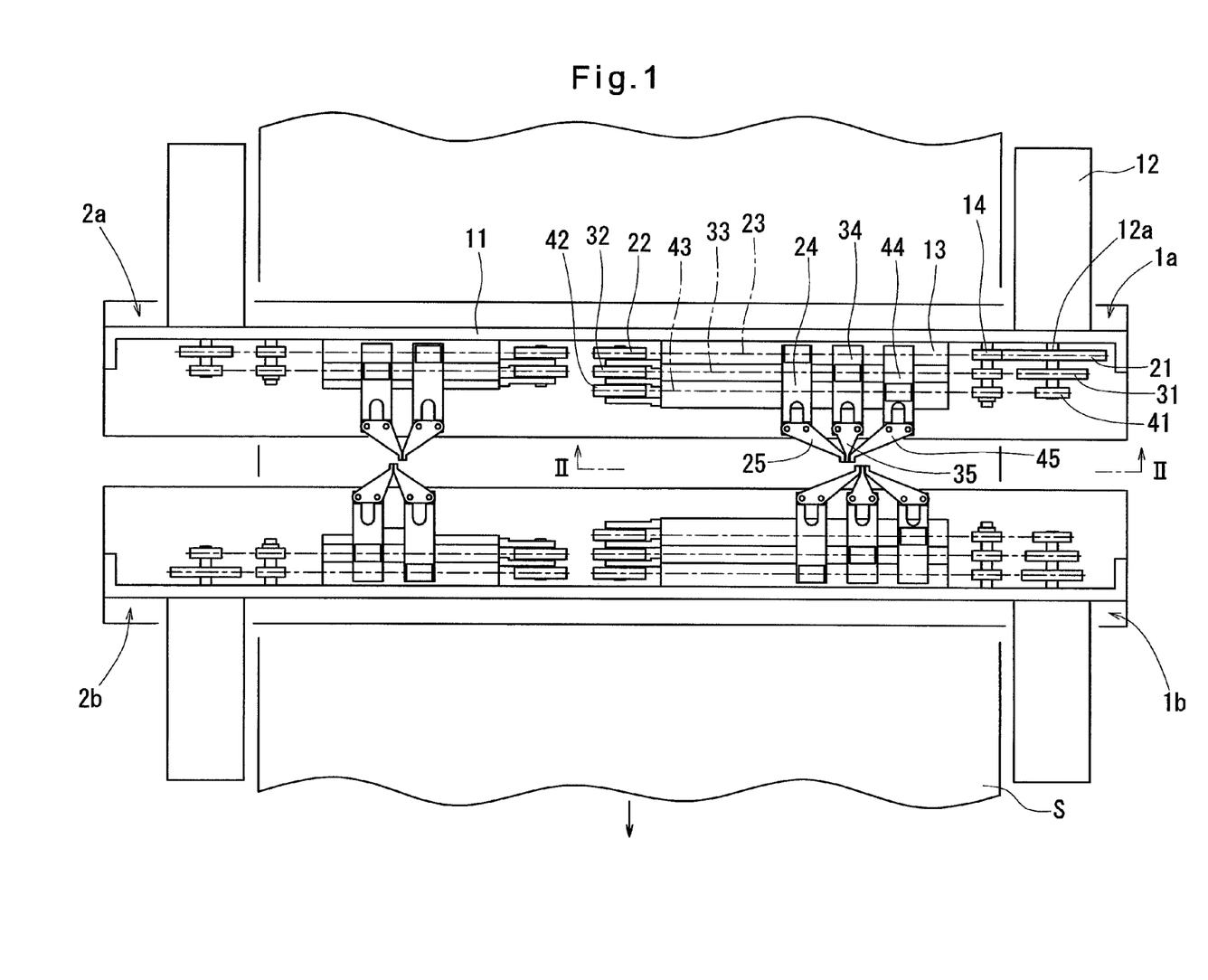
FIG. 1 is a plan view of an elastic member guide device according to an embodiment.
Figure 2:
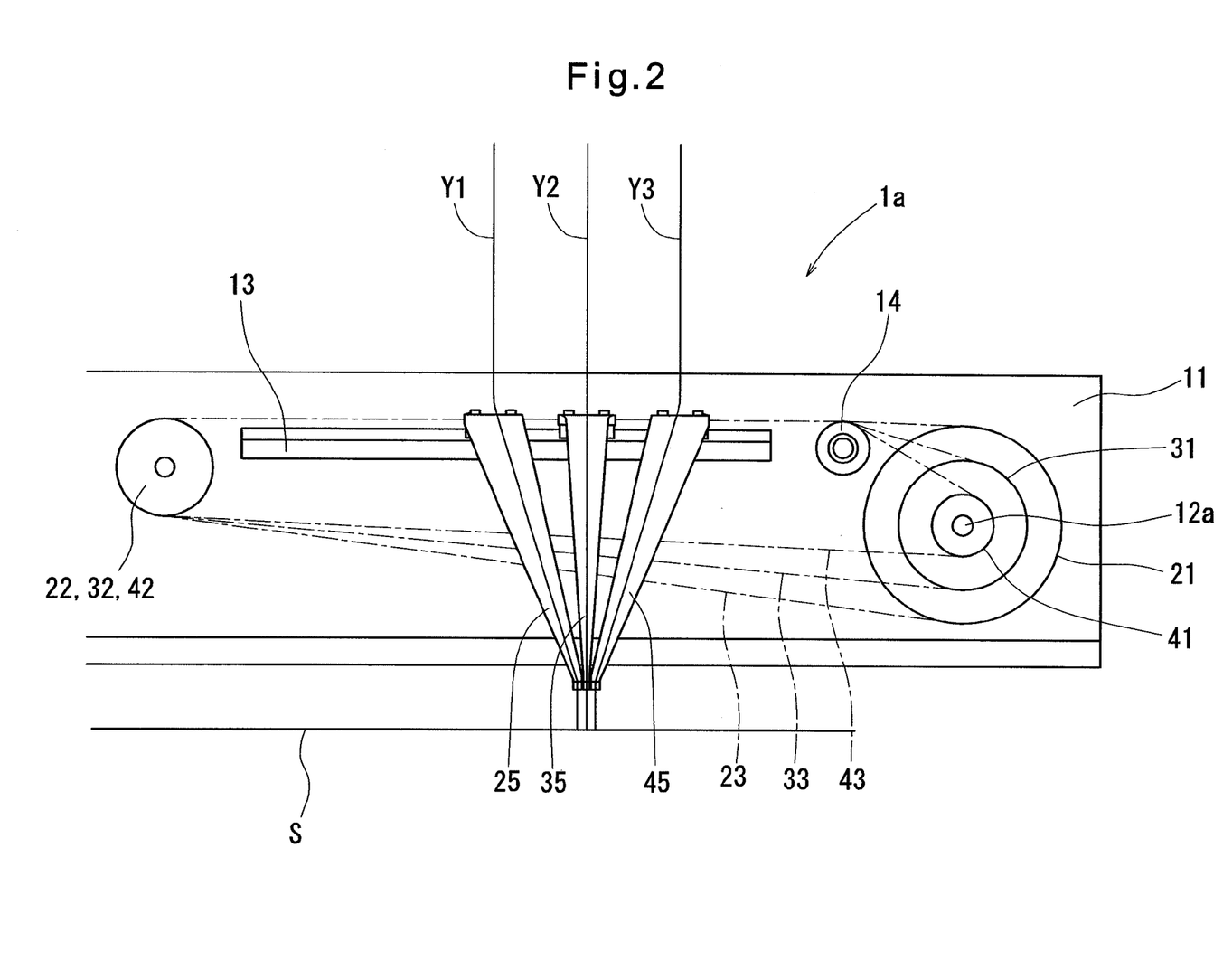
FIG. 2 is a front view of the elastic member guide device shown in FIG. 1 taken along line II-II.

As shown in FIGS. 1 and 2, an elastic member guide device 1a according to the present embodiment includes a machine casing 11 that bridges over a conveyer line of a web's one surface S, a drive shaft 12a that allows a plurality of pulleys 21, 31 and 41 to be removably attached thereto as being coaxially aligned in a rotation center axis direction, a driver portion 12 that controls the regular and reverse rotations of the drive shaft 12a, follower pulleys 22, 32 and 42 provided in a one-to-one correspondence manner relative to the pulleys 21, 31 and 41, transmission belts 23, 33 and 43 that are respectively wrapped around the pulley pairs, guide attachment and removal portions 24, 34 and 44 that are respectively provided to the transmission belts 23, 33 and 43, and guides 25, 35 and 45 that are respectively attached to the guide attachment and removal portions 24, 34 and 44. A feed direction of the web is a direction in which the web flows from upstream to downstream, which is indicated by a bottom-pointing arrow in FIG. 1. A web width direction is a direction across the web's one surface S, from one side edge to the other side edge. It is to be noted that the guide 25 and others may directly be fixed to the transmission belt 23 and others.

The drive shaft 12a is designed to allow all of the pulleys 21, 31, and 41, each having a pulley diameter falling within a prescribed range, to be aligned coaxially in the rotation center axis direction. Therefore, it is possible to set a pulley diameter ratio among the pulleys 21, 31 and 41 attached to the drive shaft 12a. The drive shaft 12a and the pulleys 21, 31 and 41 are fixed to each other by bolt fixation. It is to be noted that, so long as removable attachment of a plurality of pulleys 21, 31 and 41 coaxially aligned in the rotation center axis direction is achieved, other removal and attachment structure may be employed.

The pulley 21 and others, the follower pulley 22 and others, and the transmission belts 23, 33 and 43 can be any of the types such as flat type, V-shape type, and toothed type, so long as they are usable in an oilless manner and are capable of achieving a desired feed precision. In particular, it is preferable to employ toothed belts and pulleys for the purpose of preventing occurrence of errors due to slides.

The driver portion 12 is made up of a rotation source having a rotation axis that is coaxial to the drive shaft 12a, and a control unit that controls the rotation source. A servomotor is used as the rotation source. The control unit is configured to exert rotation speed control, rotation angle control, regular and reverse rotation switching control, and rotation start and end control, based on a well known motor control technique.

The weight of the guide attachment and removal portions 24, 34 and 44 is supported by a guide rail 13. The guide rail 13 is configured to support the guide attachment and removal portions 24, 34 and 44 so as to be in parallel to the web's one surface S, and to guide the guide attachment and removal portions 24, 34 and 44 in the web width direction of the web's one surface S.

The transmission belts 23, 33 and 43 wrapped around a plurality of pulleys 21, 31 and 41 are lifted by a guide roller 14 so as to avoid contacting with the guide rail 13. It is to be noted that the tension of the transmission belts 23, 33 and 43 can be adjusted by a not-shown well known belt tension adjustment mechanism as appropriate, in accordance with respective pulley diameters of the pulleys 21, 31 and 41 around which the transmission belts 23, 33 and 43 are respectively wrapped.

Elastic members Y1, Y2 and Y3 are passed through guide holes provided at the tip portions of the guides 25, 35 and 45, from above the web's one surface S. The elastic members Y1, Y2 and Y3 are continuously fed while maintaining an expanded state. The guides 25, 35 and 45 have their positions fixed relative to the transmission belts 23, 33 and 43 in a state where they are attached to the guide attachment and removal portions 24, 34 and 44.

The positions of the elastic members Y1, Y2 and Y3 where they are brought into contact with the web's one surface S are varied in accordance with the shift of the guides 25, 35 and 45 in the web width direction. The position variations of the guides 25, 35 and 45 in the web width direction and the contact position variation of the elastic members Y1, Y2 and Y3 correlate to each other by a prescribed precision. This is because the elastic members Y1, Y2 and Y3 are capable of being in a tense state without becoming loose and of maintaining a straight state when the guide 25 and others are shifted in the web width direction. So long as the correlation is established in a prescribed range, the manner, material and the like of the elastic members Y1, Y2 and Y3 are not specifically limited.

The guides 25, 35 and 45 shift in the web width direction along a plane that is parallel to the web's one surface S, as being guided by the guide rail 13. Accordingly, the feed amounts of the transmission belts 23, 33 and 43 are directly related to the feed amounts of the guides 25, 35 and 45 in the web width direction. Therefore, feed amount differences of the guides 25, 35 and 45 in the web width direction can easily be set based solely on the pulley diameters. That is, as to the web width direction, the interval between the elastic members Y1 and Y2 is determined by the pulley diameter ratio between the pulley 21 and the pulley 31; the interval between the elastic members Y2 and Y3 is determined by the pulley diameter ratio between the pulley 31 and the pulley 41; and the interval between the elastic members Y1 and Y3 is determined by the pulley diameter ratio between the pulley 21 and the pulley 41. When the driver portion 12 regularly rotates the drive shaft 12a, the intervals among the elastic members Y1, Y2 and Y3 vary toward one side of the web width direction; with reverse rotation, the intervals vary toward the reverse direction. It is to be noted that, it is also possible to employ a structure in which all of or part of the guides 25, 35 and 45 are provided so as to shift along a plane that is tilted relative to the web's one surface S.

For example, having the pulleys 21, 31 and 41 aligned in order of their pulley diameter size and attached to the drive shaft 12a, during the rotation of the drive shaft 12a, in accordance with the pulley diameter ratio, feed amount differences among the transmission belts 23, 33 and 43, and eventually, feed amount differences among the guides 25, 35 and 45 are generated in order of alignment. As a result, the extent of bending of the elastic member guided by one guide and that of the elastic members guided by other guides also become greater in order of alignment. The intervals in the web width direction between adjacent ones of elastic members become gradually greater in order of alignment.

Figure 3:
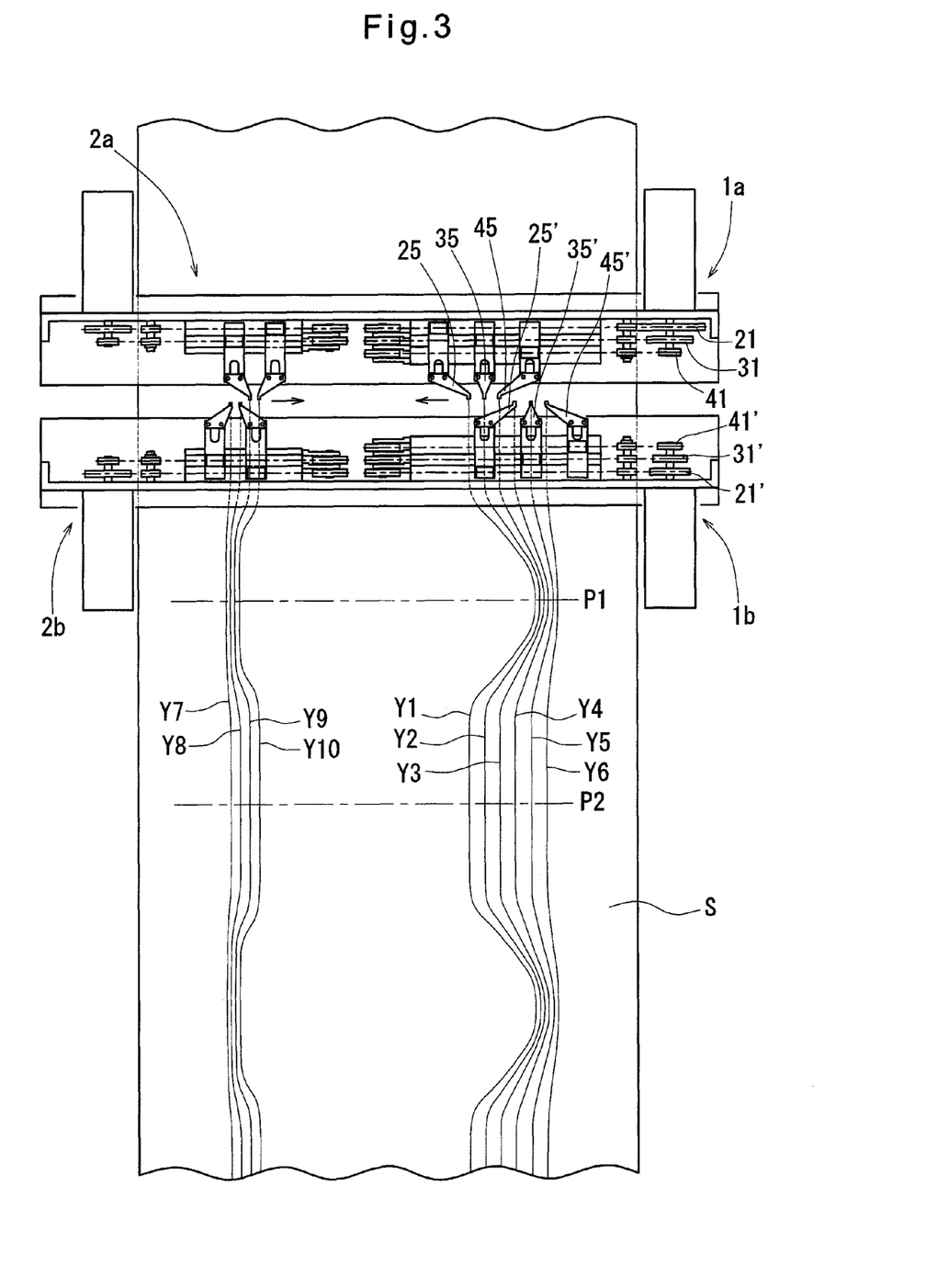
FIG. 3 is an operation diagram showing an exemplary use of the elastic member guide device shown in FIG. 1.

In the following, a description will be given of one exemplary use of the elastic member guide device according to the embodiment. As shown in FIG. 3, elastic member guide devices 1a and 1b are provided for arranging six elastic members Y1 to Y6 so as to be located closer toward one end side in the web width direction relative to the web's one surface S.

Further, elastic member guide devices 2a and 2b are provided for arranging four elastic members Y7 to Y10 so as to be located closer toward the other end side in the web width direction relative to the web's one surface S. The elastic member guide devices 1a and 1b are separately provided from the elastic member guide devices 2a and 2b, for the purpose of setting the interval width varying direction of Y1 to Y6 and that of Y7 to Y10 to be counter to each other relative to the web width direction. Because the installation space obtained above the web's one surface S is limited, the elastic member guide devices 1a and 1b are aligned in the feed direction such that respective drive shafts constitute a pair of drive shafts coaxially opposed to each other, and so are the elastic member guide devices 2a and 2b.

In the following, a description will be given taking up the elastic member guide devices 1a and 1b as an example. As compared to the elastic member guide device 1a, the elastic member guide device 1b is different in the installation direction described above, in a guide shift control direction corresponding to the difference in the installation direction, in guide initial positions, and in the pulley diameters attached to the drive shaft.

The supply source of the web is a roll of web having a constant width over the entire length. The web is configured to be unwrapped from the roll by the conveyer line and kept to be continuously fed in one direction. The web width direction in this example is perpendicular to the feed direction on the web's one surface S. This is to carry out shifting of the guides 25, 35, 45, 25', 35' and 45' in the web width direction relative to the web's one surface S in the most efficient manner, and the direction is not limited to such a perpendicular direction.

As the web, for example, one of a nonwoven fabric, a pulp sheet, a cloth, a film and the like, or a laminated material made up of layers of at least one of the aforementioned materials may be used.

The supply source of each of the elastic members Y1 to Y6 is a roll of elastic body. The elastic members Y1, Y2 and Y3 are each configured to be unwrapped from the roll by the conveyer line and kept to be continuously fed in one direction. For the purpose of easier achievement of the aforementioned correlation that falls within a prescribed range, the elastic member Y1 and others preferably have identical cross section over the entire length, and whose deformation such as twist or expansion associated with shift of the guide 25 and others in the web width direction is preferably negligible.

As the elastic member Y1 and others, for example, a rubber thread may be employed.

The elastic member Y1 and others are configured to be overlaid on an adhesive application area formed at the web's one surface S, and thereafter conveyed integrally with the web's one surface S.

The initial positions of the guides 25, 35, 45, 25', 35', and 45' correspond to the state shown in FIG. 1, in which the elastic members Y1 to Y6 are set at the positions so as to be brought into contact with line P1 shown in FIG. 3. Respective intervals in the web width direction between the elastic members Y1 and Y2, between the elastic members Y2 and Y3 ... between the elastic members Y5 and Y6 are each the minimum interval when positioned on line P1, and these positions are designated as the initial positions. Line P2 shown in FIG. 3 indicates the position where the intervals among the elastic members Y1 and Y2 and others each become the maximum interval. The values of the minimum interval and the maximum interval are identical among the pairs of the elastic members Y1 and Y2, the elastic members Y2 and Y3, ... the elastic members Y5 and Y6. The elastic members Y1 to Y6 are fixed in a wavy manner, so as to swing in the web width direction relative to the web's one surface S and to have periodicity in the feed direction.

When it is desired to fix the elastic members Y1 to Y6 as shown in FIG. 3, respective pulley diameter ratios among the pulleys 21 ... 41' should be numerically designed with reference to the feed amount that is required for the elastic members Y1 to Y6 at the minimum intervals to achieve the maximum intervals. For example, it is considered as to a case where the following is desired: each minimum interval on P1 should be 5 mm; each maximum interval on P2 should be 30 mm; and a swing of reciprocation of the elastic member Y6 between P1 and P2 in the web width direction should be 15 mm. With reference to the web width direction position of the elastic member Y6 on P1, the web width direction position of the elastic member Y5 on P2 is the position obtained by adding the maximum interval 30 mm to the swing 15 mm of the elastic member Y6. Then, the swing of the elastic member Y5 between P1 and P2 is 40 mm, which is obtained by subtracting 5 mm at the initial position on P1 from the target position on P2. In the similar manner, the swings between P1 and P2 as to the elastic members Y4 to Y1 are obtained as 65 mm, 90 mm, 115 mm, and 140 mm, respectively. The swing between each of the elastic members Y1 to Y6 can be generated by setting of the pulley diameter ratios. Specifically, the pulley diameter ratio of the pulleys 21 to 41 for the elastic members Y1 to Y3 using the same elastic member guide device 1a should be 140:115:90, the values being in order from the pulley 21. Further, the pulley diameter ratio of the pulleys 21' to 41' for the elastic members Y4 to Y6 should be 65:40:15, the values being in order from the pulley 21'. In a case where toothed belts are employed, the pulley diameter ratios may correspond to pulley tooth ratios.

As the driver portion 12 regularly rotates the drive shaft 12a from the state of minimum interval, the guides 25 and 25' and others are shifted in the left direction in FIG. 3 (from one end side in the web width direction toward the other end side). As a result, an interval widening is carried out. When the maximum intervals are reached, the driver portion 12 stops the rotation of the drive shaft 12a. Thus, arrangement regions attaining the maximum intervals are formed in the feed direction for a certain length. After a lapse of certain time therefrom, the driver portion 12 reversely rotates the drive shaft 12a, whereby the guides 25 and 25' and others are shifted in the right direction. As a result, an interval narrowing is carried out, and then the minimum intervals are recovered. When the minimum intervals are recovered, the driver portion 12 immediately switches the drive shaft 12a to carry out regular rotation, such that the maximum intervals are reached again. A series of such operations is repeatedly performed.

The extent of bending of the elastic member Y1 and others in the widening region and the narrowing region can be determined by the relationship among the pulley diameters, the rotation speed of the drive shaft 12a, and the feed speed of the web. The web is configured to be conveyed at a constant speed, so as to make it easier to set the extent of bending. The rotation speed of the drive shaft 12a is identical both in the widening region and in the narrowing region, and further, the web is conveyed at a constant speed. Therefore, the extent of bending of the elastic member Y1 and others is identical both in the widening region and in the narrowing region. As a result, on the web's one surface S, the arrangement regions achieving the maximum intervals are formed for a certain length in the feed direction at regular intervals, and the widening region and the narrowing region connecting between the maximum interval regions are formed symmetrically in the feed direction having P1 as the line-symmetrical axis.

As described above, the elastic member guide device 1*a* according to the embodiment realizes free and easy setting of the intervals such as between the elastic members Y1 and Y2 and others, based on the numerical design of the pulley diameter ratio and, regular and reverse rotation control of the drive shaft 12*a* to which the pulley 21 and others are coaxially attached. Further, because the guide 25 and others are fed in the web width direction in accordance with the pulley diameter ratio of the pulley 21 and others rotating coaxially and in synchronization with one another, the extent of bending (the displacement amount in the web width direction per unit length of the feed direction) of the elastic member Y1 and others can also be numerically designed freely and easily. Due to these characteristics, the aforementioned symmetry can exactly be obtained.

Figure 4:
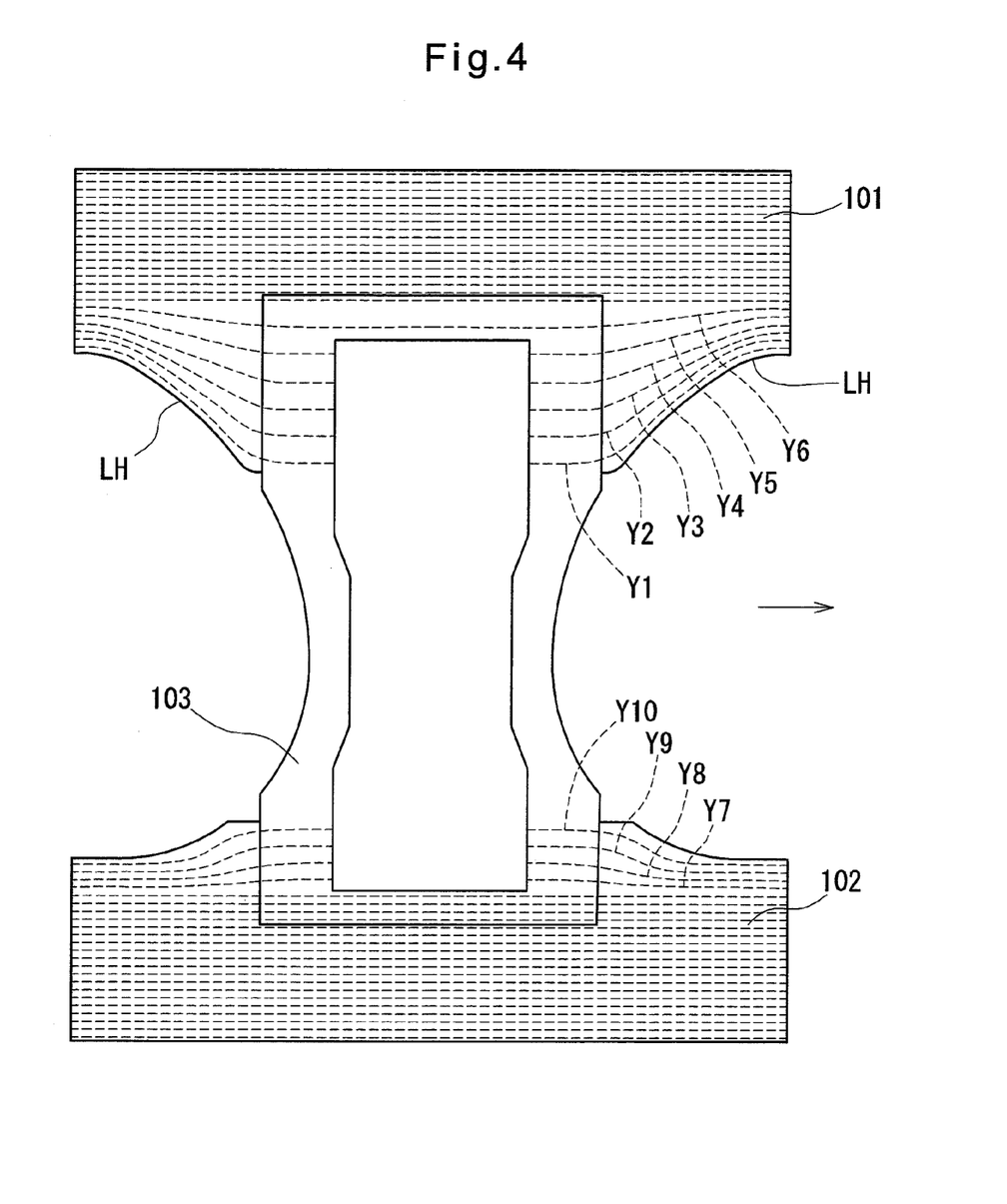
FIG. 4 is a development view of a disposable wearing article manufactured in accordance with a transverse flow manufacturing method in which the elastic member guide device according to the embodiment is employed.

A manufacturing facility of the shrinkable web shown in FIG. 3 can be used for manufacturing the disposable wearing articles. As one example thereof, a development view of a disposable wearing article manufactured by the transverse flow manufacturing method is shown in FIG. 4. The feed direction is indicated by a right-pointing arrow in FIG. 4.

A back side 101 and an abdominal side 102 of the waist portion is formed by performing a step of bonding another web so as to interpose the elastic members Y1 to Y10 between the web's one surface S, a step of intermittently cutting the elastic members Y1 to Y10 to weaken the shrinking force, and thereafter a step of cutting so as to be separated into the abdominal side and the back side. In the step of cutting, a partial back side portion of the rim portion of each leg-inserting hole LH is formed continuously to the back side 101, and a partial abdominal side portion of the rim portion of each leg-inserting hole LH is formed continuously to the abdominal side 102. Thereafter, the paralleled distance between the abdominal and back sides 101 and 102 of the waist portion is increased, and a connection member is fixed so as to connect between the abdominal and back sides 101 and 102. The connection member is formed by fixing an absorber containing defibrated fibers and the like to a cover sheet, to which cover sheet the remaining portion of the rim portion of each leg-inserting hole LH is formed. After the connection member is fixed, the developed objects each as shown in FIG. 4 are successively formed from the downstream side. By folding the developed object in the middle such that the abdominal and back sides 101 and 102 are overlaid with each other, and by joining overlapping portions on opposite sides in the feed direction, the underpants-type disposable wearing articles are successively formed from the downstream side. Thereafter, the disposable wearing articles are cut into separate pieces. As can be seen from the relationship between the developed object and the feed direction in the drawing, in the transverse flow manufacturing method, the waist portion is formed having its right to left width direction agree with the feed direction. It is to be noted that, in the transverse flow manufacturing method, in place of the step of joining the back side 101 and the abdominal side 102 of the waist portion, it is possible to perform a step of attaching any wearing tape to the developed object shown in FIG. 4, the wearing tape being for connecting between the back side 101 and the abdominal side 102 of the waist portion.

The disposable wearing article completed in the manner described above has the back side 101 and the abdominal side 102 of the waist portion, the connection portion 103, and a right and left pair of leg-inserting holes LH. The waist portion is structured as a portion where the abdominal and back sides 101 and 102 surround the waist in a circumferential direction with an identical width. The connection portion 103 is made up of the other portion continuous from the abdominal and back sides 101 and 102 and the connection member.

Cutting work to the leg-inserting holes LH loosens the web because no tension is applied to the surrounding portions. Therefore, after the elastic members Y1 to Y10 are fixed, the leg-inserting holes LH are formed. Accordingly, the site to be the rim portion of each leg-inserting hole LH is previously determined, and the elastic members Y1 to Y10 are fixed so as to avoid the sites. The cutting line of the underpants-type disposable wearing article or the developed object is line P1 in FIG. 3.

To the portion in the web's one surface S that is to be the back side 101, the elastic members Y5 and Y6 are fixed in a wavy manner, and a plurality of elastic members being parallel to the feed direction are fixed. To the portion in the web's one surface S that is to be the abdominal side 102, the elastic members Y7 and Y8 are fixed in a wavy manner, and a plurality of elastic members being parallel to the feed direction are fixed. At the abdominal and back sides 101 and 102, because there is no need to forcibly guide the elastic members fixed in parallel to the feed direction so as to be varied in the web width direction, they are fixed at another timing without using the elastic member guide devices 1*a*, 1*b*, 2*a*, and 2*b*.

To the portion in the web's one surface S that is to be the back side of the connection portion 103, the elastic members Y1 to Y4 are fixed in a wavy manner. To the portion in the web's one surface S that is to be the abdominal side of the connection portion 103, the elastic members Y9 and Y10 are fixed in a wavy manner.

The rim portion of each leg-inserting hole LH is formed such that a cut portion along the elastic members Y1 and Y10 is produced. As a result, a fit of the rim portions of the leg-inserting holes LH is enhanced by the elastic members Y1 and Y10 under the waist portion, whereby downward displacement when worn is prevented.

As in the present example, by use of the elastic member guide device 1*a* and others according to the embodiment, the elastic members Y1 to Y10 can exactly be arranged in a wavy manner with reference to the sites of the rim portions of the leg-inserting holes LH, and the fit can be enhanced.

It is to be noted that, in the present embodiment, the description has been given of the example in which the pulley 21 and others, that are different in the pulley diameter from one another, are aligned in the rotation center axis direction in order of the pulley diameter size. When the pulleys, that are identical in the pulley diameter, are aligned in the rotation center axis direction, a plurality of elastic members can constantly be kept in parallel to one another.

Further, in the present embodiment, it is also possible to set different interval values for the pairs of elastic members Y1 and Y2 and others. For example, it is possible to set the pulley diameter ratios such that the following relationship is established: the maximum interval between the elastic members Y1 and Y2<the maximum interval between the elastic members Y2 and Y3<the maximum interval between the elastic members Y3 and Y4<the maximum interval between the elastic members Y4 and Y5<the maximum interval between the elastic members Y5 and Y6. It is also possible to provide the interval variations in the reverse direction by setting the pulley diameter ratios.

Still further, in the present embodiment, it is also possible to provide two or more guide holes to each guide 25 and others, such that two or more elastic members are guided thereby. Intervals between two or more elastic members guided by one guide and two or more elastic members guided by other guide can freely and easily be set and arrangement can exactly be carried out.

Still further, in the present embodiment, because the guide 25 and others are guided by one guide rail 13, the pulley diameter ratio cannot be set such that any of the guides 25, 35 and 45 passes another guide. For example, when it is desired to have the elastic member Y1 and the elastic member Y2 intersect with each other, separate guide rails should be provided to the guide 25 and the guide 35 so as to allow one of the guide 25 and the guide 35 to pass the other, and the pulley diameter ratio between the pulley 21 and the pulley 31 should be set such that one of the guide 25 and the guide 35 passes the other.

Still further, in the present embodiment, because the elastic member guide devices 1a and 1b are provided so as to be aligned in the feed direction as shown in FIG. 3, without the necessity of providing separate guide rails as described above, it is possible to allow the elastic members to intersect with each other on the web's one surface S. For example, it is possible to allow the elastic member Y1 and others guided by the guide 25 and others belonging to one elastic member guide device 1a and the elastic member Y4 and others guided by the guide 25' and others belonging to the other elastic member guide device 1b to intersect with each other as appropriate, by the pulley diameter ratios between the pulley 21 and others and the pulley 21' and others, and rotation control of respective drive shafts. It goes without saying that the elastic members guided by different guides must be prevented from intersecting and contacting one another in the air.

Figure 5:
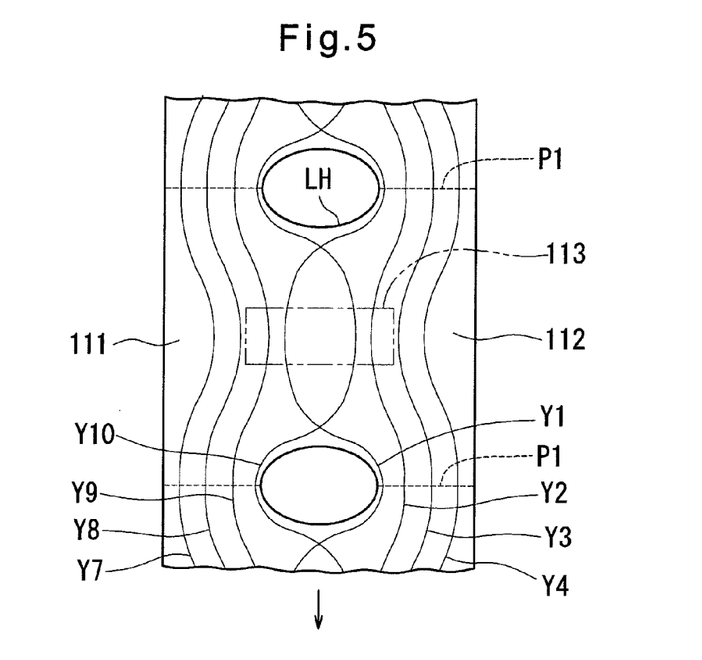
FIG. 5 is a process drawing showing an example of manufacturing other disposable wearing articles in accordance with the transverse flow manufacturing method in which the elastic member guide device according to the embodiment is employed.

For example, as in one example shown in FIG. 5, in the transverse flow manufacturing method, while abdominal and back sides 111 and 112 of the waist portion are integrally formed using the web, a web width direction intermediate portion of the web is used as the cover sheet of the connection portion, to which an absorber 113 can be fixed. The feed direction is indicated by a bottom-pointing arrow in the drawing. When the web is provided with the cover sheet portion in this manner, in fixing the elastic members Y1 to Y4 and Y7 to Y10 in a wavy manner as shown in the drawing, it becomes possible to allow the elastic member Y1 that is to be fixed at the point nearest to the rim portion of the leg-inserting hole LH as seen from one end side in the web width direction, and the elastic member Y10 that is to be fixed at the point nearest to the rim portion of the leg-inserting hole LH as seen from the other end side in the web width direction, to intersect with each other at the intermediate portion in the web width direction, so as to surround the rim portion of the leg-inserting hole LH. As a result, a fit in the entire region of the rim portion of the leg-inserting hole LH can be enhanced by the elastic members Y1 and Y10.

It is to be noted that, in the example shown in the drawing, the elastic members Y2 to Y4 and Y7 to Y9 are fixed for the purpose of enhancing the fit in the abdominal and back sides 111 and 112 of the waist portion. The elastic members Y2 to Y4 and Y7 to Y9 for such a purpose are fixed in a wavy manner, and their shrinking force is not exerted in the circumferential direction of the waist portion. However, the wavy manner of the elastic members Y2 to Y4 and Y7 to Y9 is determined such that their shrinking force chiefly acts in the circumferential direction of the waist portion. The elastic members Y2 to Y4 and Y7 to Y9 form parallel waves and the pulley diameters therefor are set to an identical value. The pulley diameters for the elastic members Y1 and Y10 that greatly swing in the web width direction are set to be considerably greater than the pulley diameters for the elastic member Y2 and others. It is to be noted that, in the example shown in the drawing, in order to allow the elastic member Y1 and the elastic member Y10 to intersect with each other, the elastic member guide device 1a and the elastic member guide device 2a cannot be disposed at the same level in the feed direction as shown in FIG. 3. The elastic member guide device 1a and the elastic member guide device 2a should be disposed as being displaced from each other in the feed direction, so as to avoid contact among the guide 25 and the others or the contact in the air between the elastic member Y1 and the elastic member Y10.

In addition to the example shown in FIG. 5, it is possible to set the pulley diameter ratio between the pulley 41 for the elastic member Y3 and the pulley 21' for the elastic member Y4, so as to feed the guide 25' to pass the guide 45, and to allow the elastic members Y3 and Y4 to intersect with each other. Further, because the guide 25 and others and the guide 25' and others do not interfere each other in the web width direction, by allowing respective drive shafts to rotate in the same direction, it becomes possible to allow at least one of the elastic members Y1 to Y3 and at least one of the elastic members Y4 to Y6 to intersect with each other.

Figure 6:
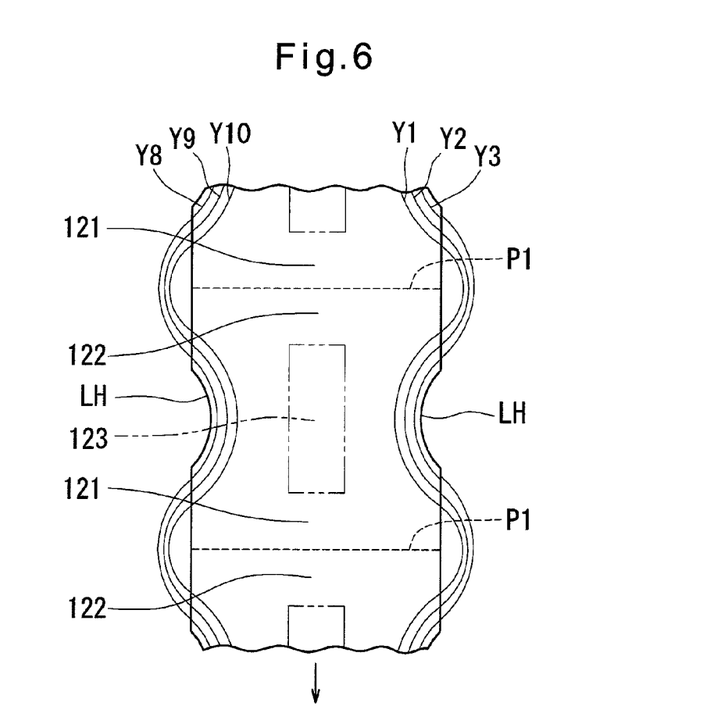
FIG. 6 is a process drawing showing an example of manufacturing disposable wearing articles in accordance with a longitudinal flow manufacturing method in which the elastic member guide device according to the embodiment is employed.

Further, the elastic member guide device 1a and others according to the embodiment can be applied also to the longitudinal flow manufacturing method. For example, as can be clearly seen from the relationship between the developed object and the feed direction (indicated by a bottom-pointing arrow in the drawing) as shown in FIG. 6, in the longitudinal flow manufacturing method, to the continuously fed web, a back side 121 and an abdominal side 122 of the waist portion are alternately formed in the feed direction having the right to left width direction of the waist portion agree with the web width direction. The intermediate portion relative to the feed direction between P1 and P1 in the web and relative to the web width direction at P1 and P1 is used as the cover sheet of the connection portion, where an absorber 123 is fixed. The rim portions of the leg-inserting holes LH are formed by partially cutting both sides in the web width direction. In the longitudinal flow manufacturing method also, the elastic members are fixed in a wavy manner for the purpose of enhancing the fit of the rim portions of the leg-inserting holes LH, the elastic member guide device 1a and others can be used. In the example shown in the drawing, as to a plurality of elastic members Y1 to Y3 and Y8 to Y10, respective swing differences between adjacent elastic members Y1 and Y2, between Y2 to Y3 and others become greater toward the center of the connection portion from the point on P1. Thus, the fit near the crotch and the rim portions of the leg-inserting holes LH where leakage of body wastes is prone to occur can drastically be enhanced, whereby the anti-leak characteristic can be improved. In order to provide the aforementioned swing differences, the pulley diameter ratios are set such that the pulley diameters are reduced in size in order of the pulleys for the elastic members Y1 and Y10, the pulleys for the elastic members Y2 and Y9, the pulleys for the elastic members Y3 and Y8.

The invention claimed is:
1. An elastic member guide device, for guiding continuously-fed elastic members in an expanded state into contact with one surface of a web being continuously fed such that the elastic members are provided to the one surface of the web at a varied interval in a web width direction, comprising:
    a drive shaft defining a first rotation center axis;
        a plurality of drive pulleys removably attached to said drive shaft so as to be coaxially aligned along the first rotation center axis;
    a follower shaft defining a second rotation center axis;
        a plurality of follower pulleys mounted on said follower shaft so as to be coaxially aligned along, the second rotation center axis;

transmission belts that are respectively wrapped around the drive pulleys and are respectively wrapped around the follower pulleys;

elastic member guides respectively fixed to said transmission belts for movement with said transmission belts, each of said elastic member guides being configured to allow one of the continuously-fed elastic members to pass therethrough to be provided to the one surface of the web;

a guide rail, said elastic member guides being guided for reciprocation along said guide rail; and a driver portion that controls regular and reverse rotations of the drive shaft, wherein a feed amount difference in the web width direction is allowed to be set for each of the elastic member guides, by determining a pulley diameter ratio among the plurality of drive pulleys.

2. The elastic member guide device according to claim 1, wherein the follower pulleys are equal in diameter, such that the feed amount difference in the web width direction is allowed to be set for each of the elastic member guides, solely by determining the pulley diameter ratio among the plurality of drive pulleys.

3. A manufacturing method of disposable wearing articles, comprising:

continuously feeding a web for forming a waist portion;

fixing elastic members that are continuously fed in an expanded state to one surface of the web in a wavy manner so as to swing in a web width direction and with a periodicity in a feed direction;

forming a rim portion of a leg-inserting hole such that a cut portion along the elastic members is generated;

wherein said fixing of the elastic members involves using the elastic member guide device according to claim 1 to guide the elastic members via the elastic member guides, respectively; and wherein the swing of each of the elastic members is set based on pulley diameters.

4. The manufacturing method according to claim 3, wherein the follower pulleys are equal in diameter, such that the feed amount difference in the web width direction is allowed to be set for each of the elastic member guides, solely by determining the pulley diameter ratio among the plurality of drive pulleys.

* * * * *